United States Patent [19]

Raible

[11] Patent Number: 4,534,761
[45] Date of Patent: Aug. 13, 1985

[54] IMPLANT DEVICE

[75] Inventor: Donald A. Raible, Irvine, Calif.

[73] Assignee: Bentley Laboratories, Inc., Irvine, Calif.

[21] Appl. No.: 539,622

[22] Filed: Oct. 6, 1983

Related U.S. Application Data

[63] Continuation of Ser. No. 292,845, Aug. 14, 1981, abandoned.

[51] Int. Cl.³ .................... A61M 31/00; A61F 1/00
[52] U.S. Cl. .................... 604/175; 128/DIG. 25; 128/1 R; 623/12
[58] Field of Search .............. 128/1 R; 3/1; 604/174, 604/175, 8

[56] References Cited

U.S. PATENT DOCUMENTS

| | | | |
|---|---|---|---|
| 3,677,795 | 7/1972 | Bokros | 427/2 |
| 3,783,868 | 1/1974 | Bokros | 3/1 X |
| 3,880,137 | 4/1975 | Bucalo | 128/1 R |
| 3,955,012 | 5/1976 | Okamura et al. | 427/2 |
| 4,217,664 | 8/1980 | Faso | 128/1 R X |

Primary Examiner—George F. Lesmes
Assistant Examiner—Nancy A. B. Swisher
Attorney, Agent, or Firm—Lyon & Lyon

[57] ABSTRACT

An implant device having a passageway, an anchor for establishing a biological anchor and a grafting mesh annularly disposed about, and spaced apart from, the exterior of the implant device. The implant device passageway, anchor means, and grafting mesh are all formed from either pyrolytic carbon disposed on a graphite substrate or vitreous carbon.

7 Claims, 4 Drawing Figures

IMPLANT DEVICE

This application is a continuation of Ser. No. 292,845, filed on Aug. 14, 1981, now abandoned.

BACKGROUND OF THE INVENTION

The present invention relates to an implant device.

There are many situations in which it is necessary to perform an enterostomy on a patient. An enteroostomy involves externalizing an internal vessel. Common vessels which commonly require externalizing are the ileum, colon, ureter, and bladder. Heretofore, enterostomies were accomplished by severing the vessel which was to be externalized and then suturing the wall of the vessel to an opening which has been formed on the surface of the body. The opening is normally formed on the abdomen. Generally, the wall of the vessel and the dermis of the skin surrounding the opening will grow together to permanently secure the vessel to the surface of the body. After the operation has healed, a container is attached to the surface of the skin. The container functions to receive the excrements which are discharged from the vessel. These excrements may be acidic due to the pressure of enzymes et cetera, and when they contact the surface of the skin, they cause ulceration. For example, in an ileostomy, the ileum is externalized to the abdomen of the patient and the enzymes, fecal material, et cetera, which exit from the ileum cause ulceration of the skin surrounding the point of externalization. This is primarily due to the presence of active enzymes in the small intestines.

Further, there are a number of situations in which it is necessary to provide for fluid communication with the vascular system. For example, patients suffering from kidney failure require the dialysis of their blood by means external from the body. Blood containing toxic substances, such as urea, uric acid, creatine, phosphorous and calcium, must be removed from the blood system, treated and then returned to the patient. Patients requiring such blood dialysis require treatment at least two or three times per week. Patients suffering from hypoalimentation require a device for providing access to the body's vascular system on at least a daily basis.

One prior method of providing fluid communication with the vascular system involved the insertion of a needle into an artery from which blood to be treated was taken and the insertion of a needle into a patient's vein for blood return. Such a method proved unsatisfactory due to the difficulty in providing for the healing of the artery upon removal of the needle and the trauma produced by the repeated needle insertions. Such shortcomings led to the development of external and, later internal shunts.

An external shunt involves the insertion of the tubes, such as those made of Teflon, into an artery and an adjacent vein in a limb and providing an external communication or shunt between the tubes, which extend from the body of the patient. The shunt between the tubes is required in order to provide flow through the tubes during that period of time that access is not required for blood treatment. Where such circulating blood flow not provided, a blood clot or thrombus could form as would be the case if the tubes were simply capped creating a static blood volume when the tubes were not in use. Dialysis, for example, is accomplished by connecting the arterial and venous tubing to a suitable dialysis unit. However, such a configuration traumatizes the skin adjacent the Teflon tubes and a path is provided through the skin for infection to enter the patient's body. Furthermore, even with external shunts, blood clots sometimes form within the tubes and create a health hazard to the patient.

The disadvantages of external shunts led to the development of the internal shunt. An internal shunt is performed by joining, within a body, openings between an artery and an adjacent vein, thereby forming a fistula. One or two needles were then inserted into the fistula in order to achieve communication with the patient's vascular system. The patient suffers major discomfort and pain each time the needles are inserted in the fistula. Moreover, the continous intrusion into the fistula causes it to become layered with scar tissue which ultimately prevents further intrusion, thus requiring the formation of another shunt.

Both the internal and external shunts increase the loading on the patient's heart due to the joining of the artery to a vein having a lower pressure, thereby lowering the artery's pressure, and requiring the heart to attempt to regain the original arterial blood pressure. Further, in many cases, the reduced circulation in the distal portion of the limb wherein the shunt is effected impairs the adequate perfusion of blood.

DESCRIPTION OF PREFERRED EMBODIMENTS

Figure 1:
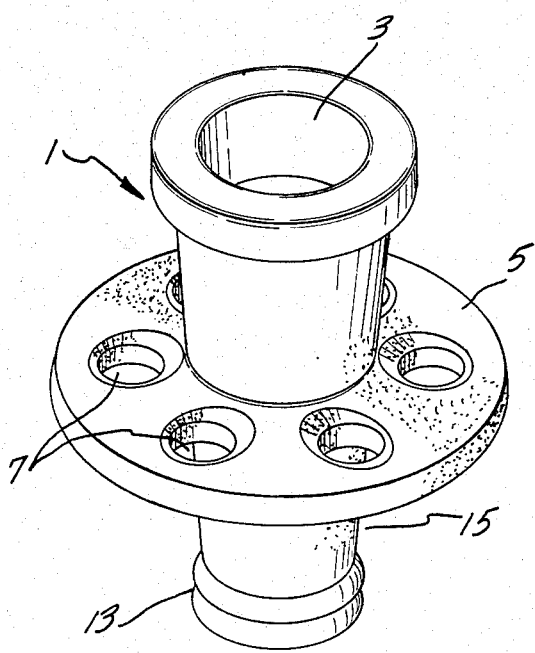
FIGS. 1 and 2 are pictorial views of the implant device of this invention.
Figure 2:
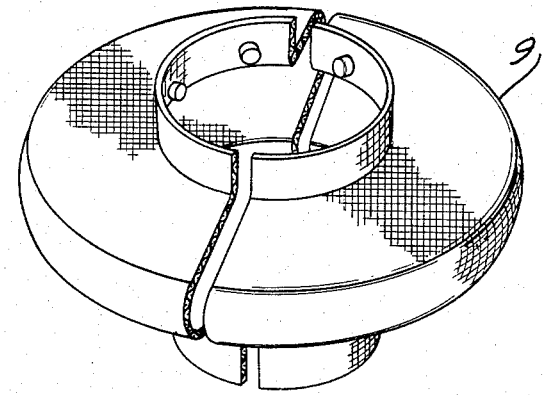
Figure 3:
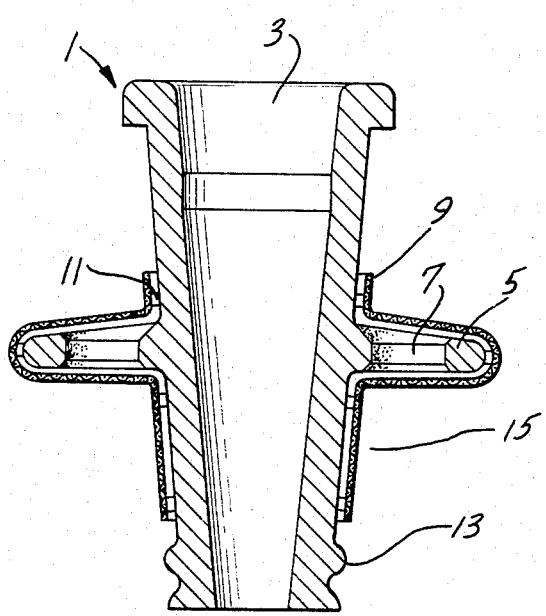
FIG. 3 is a cross-sectional view of the implant device of the present invention.
Figure 4:
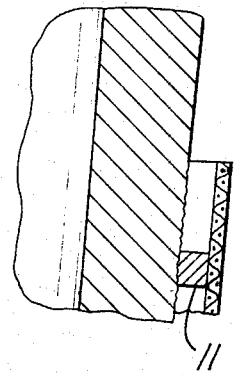
FIG. 4 is a partial cross-sectional view of the implant device of the present invention.

Referring now to FIG. 1, the implant device of this invention, generally referred to as 1, will be discussed. The implant device 1 includes a passageway 3 extending therethrough and an anchor means 5 for establishing a biological anchor. Anchor means 5 preferably includes a plurality of apertures 7 extending therethrough.

Implant device 1 also includes an annular rim 13 which forms an annular recess 15 between the annular rim 13 and the anchor means 5.

A valved implant device of the type for which drafting mesh 9, later described, is adopted for use therewith is that described in issued U.S. Pat. No. 4,164,221, issued Aug. 14, 1979 of which the inventor of this invention was a coinventor and hereby incorporated by reference.

Grafting mesh 9 is positioned annularly about at least a portion of the exterior of the implant device 1. The grafting means mesh 9 is spaced apart from the implant device 1 as, for example, by means of a spacer 11 in order to allow for tissue ingrowth between the implant device 1 and the grafting mesh 9. In a preferred embodiment the exterior of the implant device 1 is roughened in order to promote tissue coaption.

The implant device passageway, anchor means and grafting mesh are formed from either pyrolytic carbon disposed on a graphite substrate or vitreous carbon. Preferably the grafting mesh and the exterior of the implant device are coated with collagen.

What is claimed is:

1. An implant device comprising:
   a passageway having an anchor means, both of which are formed from a material selected from the group consisting of (1) pyrolytic carbon disposed on a graphite substrate of (2) vitreous carbon, for attachment to an opened vessel;

said anchor means for establishing a biological anchor;

a grafting mesh annularly and longitudinally disposed about at least a portion of the exterior of said implant device, said grafting mesh being formed from a material selected from the group consisting of (1) pyrolytic carbon disposed on a graphite substrate or (2) vitreous carbon; and means for radially and longitudinally spacing said grafting mesh away from the exterior of said implant device such that tissue is permitted to grow between the exterior of said implant device and said mesh longitudinally on both sides of said space means.

2. The implant device claimed in claim 1 wherein the exterior of said implant device is roughened in order to provide a plurality of interstices in order to facilitate tissue coaption.

3. The implant device claimed in claim 1 wherein an annular rim is positioned about said passageway thereby forming an annular recess between said annular rim and said anchor means.

4. The implant device claimed in claim 1 wherein at least a portion of the exterior of said implant device is coated with collagen.

5. The implant device claimed in claim 1 wherein at least a portion of said grafting mesh is coated with collagen.

6. An implant device comprising:

a passageway having an anchor means, both of which are formed from a material selected from the group consisting of (1) pyrolytic carbon disposed on a graphite substrate or (2) vitreous carbon, for attachment to an opened vessel;

said anchor means for establishing a biological anchor, and the exterior of said implant device being roughened in order to provide improved coaption;

an annular rim is positioned about said passageway thereby forming an annular recess between said annular rim and said anchor means;

a grafting mesh annularly and longitudinally disposed about at least a portion of the exterior of said implant device, said grafting mesh being formed from a material collected from the group consisting of (1) pyrolytic carbon disposed on a graphite substrate or (2) vitreous carbon; and means for radially and longitudinally spacing said grafting mesh away from the exterior of said implant device such that tissue is permitted to grow between the exterior of said implant device and said mesh longitudinally on both sides of said space means.

7. The implant device claimed in claim 6 wherein said grafting mesh and at least a portion of the exterior of said implant device are coated with collagen.

* * * * *